(12) United States Patent
Ying et al.

(10) Patent No.: US 11,591,310 B2
(45) Date of Patent: Feb. 28, 2023

(54) METHOD FOR PREPARING LENALIDOMIDE

(71) Applicant: SHANGHAI BOCIMED PHARMACEUTICAL CO., LTD., Shanghai (CN)

(72) Inventors: Shuhuan Ying, Shanghai (CN); Yuhui Guo, Shanghai (CN); Jian Chen, Shanghai (CN); Tingting Wang, Shanghai (CN)

(73) Assignee: SHANGHAI BOCIMED PHARMACEUTICAL CO., LTD., Shanghai (CN)

( * ) Notice: Subject to any disclaimer, the term of this patent is extended or adjusted under 35 U.S.C. 154(b) by 121 days.

(21) Appl. No.: 15/734,122

(22) PCT Filed: Feb. 11, 2019

(86) PCT No.: PCT/CN2019/074799
§ 371 (c)(1),
(2) Date: Dec. 1, 2020

(87) PCT Pub. No.: WO2019/227968
PCT Pub. Date: Dec. 5, 2019

(65) Prior Publication Data
US 2021/0214334 A1 Jul. 15, 2021

(30) Foreign Application Priority Data
Jun. 1, 2018 (CN) .......................... 201810558327.9

(51) Int. Cl.
*C07D 401/04* (2006.01)
(52) U.S. Cl.
CPC ........ *C07D 401/04* (2013.01); *C07B 2200/13* (2013.01)
(58) Field of Classification Search
CPC .................................................. C07D 401/04
See application file for complete search history.

(56) References Cited

FOREIGN PATENT DOCUMENTS

| CN | 103601717 A | 2/2014 | |
|---|---|---|---|
| CN | 104311536 A | 1/2015 | |
| CN | 106957299 A | 7/2017 | |
| CN | 107033126 A | 8/2017 | |
| CN | 107337666 A | 11/2017 | |
| WO | 2011050962 A1 | 5/2011 | |
| WO | WO-2016026785 A1 * | 2/2016 | ........... C07D 401/04 |

OTHER PUBLICATIONS

Yin, Jingmei et al., Research Progress in Preparation of Aromatic Amine via Reduction of Aromatic Nitro Compounds; Chemical Research; vol. 21, No. 1, Jan. 2010, 1008-1011, pp. 96-101.

Wu, Jia-Wei et al.; "Research Progress of Preparing o-or p- Chloro Anline from o- or p- Chloro Nitro Benzene"; Journal of Lanzhou Petrochemical College of Technology; vol. 10, No. 3; Sep. 15, 2010; pp. 1-4.

Cao, Ge et al.; "Advances in Process for the Selective Reduction of Nitroarenes to the Corresponding Aromatic Amines"; Modern Chemical Industry; vol. 31, No. S1; Jun. 30, 2011; pp. 57-62.

Giulietti, Marco et al.; "Industrial Crystallization and Precipitation From Solutions: State of the Technique"; Brazilian Journal of Chemical Engineering; vol. 18, No. 4; Dec. 1, 2001; ISSN: 0104-6632; pp. 423-440.

Chinese Patent Office, office action of counterpart application CN 201910110248.6, dated Apr. 29, 2020.

(Continued)

*Primary Examiner* — Sikarl A Witherspoon
(74) *Attorney, Agent, or Firm* — Novick, Kim & Lee, PLLC; Allen Xue

(57) ABSTRACT

The present disclosure discloses a method for preparing lenalidomide. The present disclosure provides a method for preparing lenalidomide I, which comprises the following steps: in a solvent, the lenalidomide intermediate II is reduced with a metal in the presence of an organic acid to obtain the lenalidomide I, wherein the metal is one or more selected from zinc, iron, aluminum and manganese. The preparation method of the disclosure has simple and safe operation, simple post-processing steps, environmental friendliness, high total yield. Moreover, the product obtained in the method has a purity of more than 99.90%, maximum single impurity of less than 0.10%, total heavy metal residue of less than 10 ppm and meet the heavy metal residue standard and API standard. Furthermore, the method has a low production cost and is suitable for industrial production.

9 Claims, No Drawings

(56) References Cited

OTHER PUBLICATIONS

Chinese Patent Office, office action of counterpart application CN 201910110248.6, dated Nov. 4, 2020.
European Patent Office, office action of counterpart application EP 19811339.1, dated May 18, 2021.

* cited by examiner

METHOD FOR PREPARING LENALIDOMIDE

This application is a U.S. national phase entry of International application no. PCT/CN2019/074799, filed Feb. 11, 2019, which claims the benefit of and priority to the prior Chinese patent application No. 201810558327.9, entitled "METHOD FOR PREPARING LENALIDOMIDE" and filed before the Chinese National Intellectual Property Office on Jun. 1, 2018, which is hereby incorporated by reference in its entirety.

TECHNICAL FIELD

The present disclosure relates to a method for preparing Lenalidomide.

BACKGROUND

Lenalidomide (Lenalidomide, I) is a new generation of anti-tumor drug developed by Celgene Biopharmaceutical Corporation in the United States, it is mainly used to treat myelodysplastic syndrome and multiple myeloma. On Dec. 27, 2005, FDA approved the lenalidomide capsules developed by Celgene to market through a rapid approval process. On Jun. 29, 2006, FDA approved lenalidomide combined with dexamethasone for the treatment of multiple myeloma patients who had previously received at least one treatment. As a first-line treatment of multiple myeloma, lenalidomide has been widely recognized by doctors and patients worldwide.

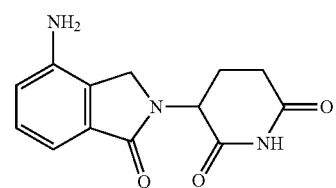

lenalidomide I was generally obtained as follows: lenalidomide intermediate II is synthesized by condensation of methyl 2-bromomethyl-3-nitrobenzoate and 3-amino-2,6-piperidinedione hydrochloride, and then reduced to lenalidomide I. The synthesis methods that have been reported under the existing technical conditions include patent literature WO2011050962 and so on.

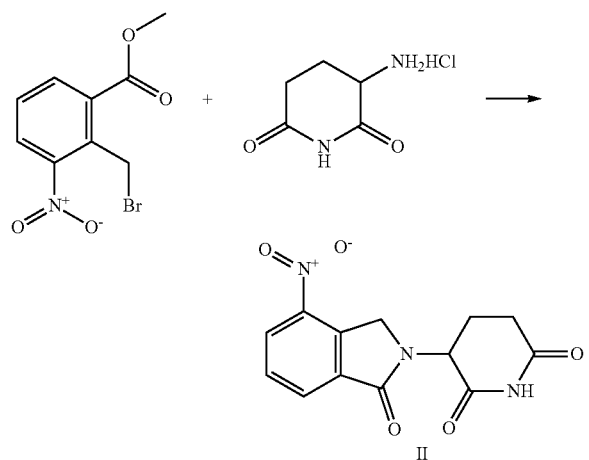

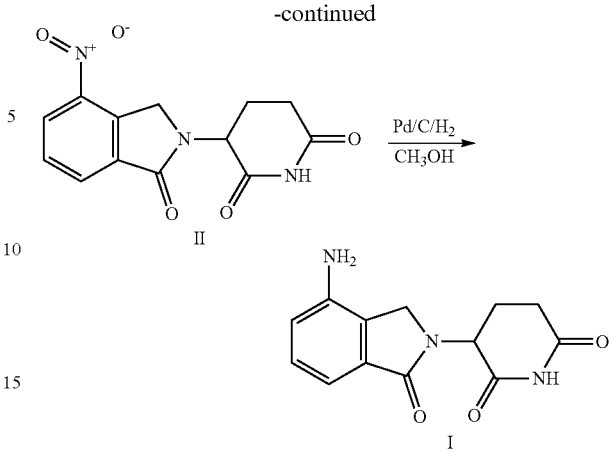

In the above method, mental palladium catalyst was used for reduction hydrogenation, so that the residue defects of the metal palladium in the final product obtained in this process were relatively serious (39 ppm). Accordingly, additional steps to remove the metal palladium were necessary, accompany with low yield (total yield 55%) and increased production costs. In addition, the catalytic hydrogenation of the metal palladium requires a special equipment, which also limits the industrial production of lenalidomide. Therefore, it is necessary to find a method with simple operation, low cost and high yield for the preparation of lenalidomide I with high-purity and adapt to the needs of industrial production.

SUMMARY OF THE DISCLOSURE

The technical problem aimed to be solved by the present disclosure is to provide a method for preparing lenalidomide, so as to improve the preparation methods of lenalidomide in the prior art which have the problems of harsh reaction condition, high production equipment requirement, high operation risk, serious environmental pollution, cumbersome post-processing steps, low yield, low product purity, high residue of heavy metals, high production cost, unsuitable for industrial production and other defects. The method of the present disclosure has the advantages such as simple and safe operation, simple post-processing steps and environmental friendliness. Moreover, the present method can achieve a product with high total yield, high purity and low residue of heavy metal to meet the API (active pharmaceutical ingredient) standard. Furthermore, present preparation method has a low production cost and is suitable for industrial production.

The present disclosure provides a method for preparing lenalidomide I, comprising the following steps: in the presence of an organic acid, the lenalidomide intermediate II is reduced with a metal to obtain the lenalidomide I, wherein the metal is one or more selected from zinc, iron, aluminum and manganese:

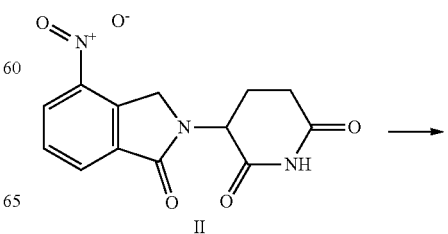

-continued

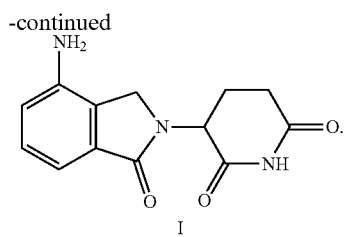

According to an embodiment of the present disclosure, the reaction is preferably carried out in a solvent.

According to an embodiment of the present disclosure, the method for preparing lenalidomide I comprises the following steps: in the presence of an organic acid, the lenalidomide intermediate II is reduced with a metal in a solvent to obtain the lenalidomide I, wherein the metal is one or more selected from zinc, iron, aluminum and manganese.

Preferably, the method for preparing lenalidomide I is carried out under the protection of a protective gas, wherein the protective gas is preferably selected from nitrogen and/or argon.

According to the method for preparing lenalidomide I, the solvent is preferably selected from an alcohol solvent or a mixed solvent of an alcohol solvent and water, wherein the alcohol solvent is preferably one or more selected from methanol, ethanol, isopropanol, n-propanol and n-butanol, further preferably one or more selected from n-propanol, isopropanol and ethanol. Where the solvent used in the method is the mixed solvent of an alcohol solvent and water, the volume ratio of the alcohol solvent to water is preferably 0.1 to 10, further preferably 0.5 to 3, and more preferably 0.5 to 2.5, such as 0.7, 1.4, 1.5, 2.1 or 1.

According to the method for preparing lenalidomide I, the volume-mass ratio of the solvent to the lenalidomide intermediate II is preferably 1 mL/g~50 mL/g, further preferably 5 mL/g~25 mL/g, more preferably 10 mL/g~25 mL/g, such as 17 mL/g, 22 mL/g or 14 mL/g.

According to the method for preparing lenalidomide I, the organic acid is preferably unsubstituted $C_{1-6}$ alkyl carboxylic acid, further preferably one or more selected from formic acid, acetic acid and propionic acid.

According to the method for preparing lenalidomide I, the molar ratio of the metal to the lenalidomide intermediate II is preferably 1-10, more preferably 3-8, such as 4.5, 7.6 or 3.5.

According to the method for preparing lenalidomide I, the molar ratio of the organic acid to the lenalidomide intermediate II is preferably 1-30, more preferably 7-15, such as 10.1, 14.8, 10.4 or 7.4.

According to the method for preparing lenalidomide I, the temperature of the reduction reaction is preferably 55° C. to 95° C., further preferably 60° C. to 90° C., such as 75° C. to 85° C., 65° C. to 75° C. or 70° C. to 80° C.

According to the method for preparing lenalidomide I, the progress of the reduction reaction can be monitored with a known monitoring method in the art (such as TLC, HPLC or NMR), wherein generally the end point of the reaction can be confirmed where the lenalidomide intermediate II disappears. The time of the reduction reaction is preferably 1 hour to 16 hours, more preferably 1 hour to 5 hours, such as 1 hour to 2 hours, 3 hours to 4 hours or 2 hours to 3 hours.

The method for preparing lenalidomide I preferably adopts the following post-processing steps: after the reaction, the crude product of lenalidomide I is obtained by filtering and washing. Optionally, the preferred the post-processing steps comprise cooling crystallization after the filtration is completed. Preferably, the filtration is a hot filtration, wherein the temperature of the hot filtration is preferably 55° C. to 95° C., more preferably 60° C. to 90° C., such as, 75° C.-85° C., 65° C.-75° C., or 70° C.-80° C. The temperature of the cooling crystallization is preferably −5° C.-35° C., more preferably 5° C.-30° C., such as, 15° C.-20° C. The time of the cooling crystallization is preferably 0.1-5 hours, more preferably 0.2-3 hours, for example 1 hour to 2 hours. The washing is preferably carried out with an alcohol solvent and/or water. The alcohol solvent is preferably one or more selected from methanol, ethanol, isopropanol, n-propanol and n-butanol. The volume-to-mass ratio of the solvent used for washing to the lenalidomide intermediate II is preferably 0.1 mL/g to 10 mL/g, further preferably 0.5 mL/g to 5 mL/g, more preferably 0.5 mL/g to 2 mL/g, such as 1.0 mL/g or 1.3 mL/g. Where the solvent used for the washing is a mixed solvent of the alcoholic solvent and water, the volume ratio of the alcoholic solvent to water is preferably 0.1 to 10, further preferably 0.5 to 3, more preferably 0.5 to 2.5, such as, 0.7, 1.4, 1.5, 2.1 or 1. The number of the washing times can be 1 to 3 times, such as 2 times.

Preferably, the crude product of lenalidomide I is further recrystallized to obtain the lenalidomide I. The solvent used for the recrystallization is preferably an alcohol solvent or a mixed solvent of an alcohol solvent and water, wherein the alcohol solvent is preferably one or more selected from methanol, ethanol, isopropanol, n-propanol and n-butanol, further preferably isopropyl alcohol and/or ethanol. The volume-mass ratio of the solvent used in the recrystallization to the lenalidomide intermediate II is preferably 1 mL/g~50 mL/g, further preferably 3 mL/g~20 mL/g, such as 12 mL/g or 4.4 mL/g. Where the solvent used in the recrystallization is the mixed solvent of an alcohol solvent and water, the volume ratio of the alcohol solvent to water in the mixed solvent is preferably 0.1 to 10, further preferably 0.5 to 3, such as, 0.7, 1.4, 1.5, 2.1 or 1. Temperature of the recrystallization is preferably 55° C. to 95° C., further preferably 60° C. to 90° C., such as, 75° C. to 85° C., 65° C. to 75° C., or 70° C. to 80° C.

According to the present disclosure, an organic acid and activated carbon are preferably added in the recrystallization. The organic acid is preferably one or more selected from formic acid, acetic acid and propionic acid; further preferably formic acid and/or acetic acid.

The recrystallization preferably adopts the following steps: in a solvent, the crude product of lenalidomide I is heated and dissolved together with activated carbon and an organic acid, filtered, cooling crystallized, washed and dried to obtain the lenalidomide I.

Preferably, in the recrystallization step, the mass ratio of the activated carbon to the lenalidomide intermediate II is preferably 0.01 to 1, more preferably 0.03 to 0.5, further preferably 0.05 to 0.5, such as 0.1.

Preferably, In the recrystallization step, the molar ratio of the organic acid to the lenalidomide intermediate II is preferably 1-10, further preferably 5-8, more preferably 7-8, for example 7.6 or 7.5.

Preferably, In the recrystallization step, the temperature of the heating and dissolving is preferably 55° C. to 95° C., further preferably 60° C. to 90° C., such as 75° C. to 85° C., 65° C. to 75° C. or 70° C.-80° C. The time of the heating and dissolving is preferably 1 hour to 5 hours, more preferably 2 hours to 4 hours, for example, 2 hours to 3 hours or 1 hour to 2 hours. The temperature of the cooling crystallization is preferably −5° C. to 35° C., more preferably 5° C. to 30° C., for example, 15° C. to 20° C. The time of the cooling crystallization is preferably 0.1-5 hours, more preferably 0.2-3 hours, for example 0.5-1 hour. The dissolution, filtration, washing, and drying can be performed with a known method in the art. The filtering is preferably hot filtration; wherein the temperature of the hot filtration is preferably 55° C. to 95° C., further preferably 60° C. to 90° C., such as 75° C. to 85° C., 65° C. to 75° C. or 70° C. to 80° C. The washing solvent is preferably an alcohol solvent or a mixed solvent of an alcohol solvent and water. The alcohol solvent is preferably one or more selected from methanol, ethanol, isopropanol, n-propanol, and n-butanol, and further preferably isopropanol and/or ethanol. The volume-mass ratio of the solvent used in the washing to the lenalidomide intermediate II is preferably 1 mL/g~50 mL/g, further preferably 1 mL/g~25 mL/g, such as 1.0 mL/g, 2.1 mL/g, 2.4 mL/g, 5.6 mL/g, 10.3 mL/g or 21.3 mL/g. Where the mixed solvent of an alcohol solvent and water is used, the volume ratio of the alcohol solvent to water in the mixed solvent is preferably 0.1 to 10, more preferably 0.5 to 3, such as 0.7, 1.3, 1.4, 1.5, or 2.1. The number of washing times is preferably 1 to 3 times, such as, 2 times. The drying is preferably vacuum drying; the temperature of the vacuum drying is preferably 55° C. to 65° C.; the time of the vacuum drying is preferably 12 hours to 16 hours; the pressure of the vacuum drying is preferably −0.01 MPa to −0.1 MPa.

According to the present disclosure, the single-step yield of the method is higher than 86.0%; such as 90.1%, 90.3%, 86.8%, 88.7% or 87.3%, and the total yield is higher than 76.0%, such as 79.1%, 79.4%, 76.2%, 77.8% or 76.6%.

According to the present disclosure, the lenalidomide I prepared by the present method has a purity of more than 99.90%, a maximum single impurity of less than 0.10%, and a total heavy metal residue of less than 10 ppm, which meets the standards of API. Preferably, the lenalidomide I has a residue of metallic chromium and metallic cadmium less than 1 ppm. For example, HPLC purity is 99.96%, the maximum single impurity is 0.03%, the total heavy metal residue is less than 10 ppm, metal zinc residue is 5 ppm, metal cadmium residue is less than 1 ppm; for example, the HPLC purity is 99.96%, the maximum single impurity is 0.04%, the total heavy metal residue is less than 10 ppm, metal iron residue is 6 ppm, the metal chromium residue is less than 1 ppm; for example, the HPLC purity is 99.95%, the maximum single impurity is 0.03%, the total heavy metal residue is less than 10 ppm, the metal zinc residue is 4 ppm, the metal cadmium residue is less than 1 ppm; for example, the HPLC purity is 99.92%, the maximum single impurity is 0.05%, the total heavy metal residues is less than 10 ppm, the metal zinc residues is 5 ppm, the metal cadmium residues is less than 1 ppm; for example, the HPLC purity is 99.91%, the maximum single impurity is 0.05%, the total heavy metal residues is less than 10 ppm, the metal aluminum residue is 15 ppm; or, for example, the HPLC purity is 99.87%, the maximum single impurity is 0.06%, the total heavy metal residue is less than 10 ppm, the metal manganese residue is 6 ppm.

Without deviating from the common knowledge in the art, the above-mentioned preferred conditions can be discretionarily combined to obtain preferred embodiments of the present disclosure.

All the reagents and raw materials used in the present disclosure are commercially available. As an example, where the metal used is selected from iron powder, the mass percentage content of metal chromium is about 0.1%. Preferably, the iron powder does not contain metal cadmium. Where the metal used is selected from zinc powder, the mass percentage content of metal cadmium is about 0.1%. Preferably, the zinc powder does not contain metallic chromium.

In the present disclosure, the room temperature refers to an ambient temperature, which is 10° C. to 35° C.

Advantageous Effect of the Present Disclosure

The method of the present disclosure has simple and safe operation, simple post-processing steps, environmental friendliness, high total yield (85% or more). Moreover, the product obtained in the method has a high purity (purity of more than 99.90%, maximum single impurity of less than 0.10%, total heavy metal residue of less than 10 ppm) and meet the heavy metal residue standard and API standard. Furthermore, the method has a low production cost and is suitable for industrial production.

DETAILED DESCRIPTION

The preparation method and application of the disclosure will be further described in detail in combination with specific embodiments. The following examples are merely illustrative of the present disclosure and are not to be construed as limiting the scope of the present disclosure. The technology that is implemented based on the above-described contents of the present disclosure is encompassed within the scope of the present disclosure.

Unless otherwise specified, all the raw materials and reagents used in the following examples are commercially available or can be prepared by known methods.

Example 1: Preparation Method of Lenalidomide Intermediate II (Referring to the Method of Patent Literature WO2011050962)

7.0 L of N,N dimethylformamide was added into a 20 L reactor, and methyl 2-bromomethyl-3-nitrobenzoate (1.5 kg, 5.47 mol) and 3-amino-2,6-piperidinedione hydrochloride (1.0 kg, 6.07 mol) were added under stirring. Then sodium bicarbonate (1.5 kg, 14.1 mol) was added. The system was heated to 50° C.~60° C. and stirred for 23 hours, then cooled down to 30~40° C. Into another 30 L reactor, 18 L of purified water was added, the previously obtained reaction solution was added in batches, cooled to 15° C.~20° C. and stirred, rested, and filtered. Into a 30 L reactor, 22 L of purified water was added, the filter cake previously obtained was added under stirring, stirred at 15° C.~25° C. for 0.5 hour, filtered, and then the filter cake was washed with 7.5 L of purified water and drained. Into a 20 L reactor, 15 L of ethyl acetate was added, and the filter cake was added under stirring, stirred at 15° C.~25° C. for 0.5 hours, filtered, and the filter cake was washed with 2.5 L of ethyl acetate and drained, vacuum dried (45° C.~55° C., −0.01 MPa~0.1 MPa) for 8~12 hours, to give 1.39 kg of off-white solid lenalidomide intermediate II, with a yield of 87.8% and a purity of 99.84%.

Example 2: Preparation Method of Lenalidomide I 5.46 L of purified water, acetic acid (1.64 kg, 27.3 mol) and 7.8 L of isopropanol were added into a 30 L reactor, stirred. 0.78 kg of lenalidomide intermediate II (2.70 mol, HPLC purity of 99.84%) and zinc powder (0.79 kg, 12.1 mol, in which the mass percentage content of metal cadmium is about 0.1%) were added into the above reactor, and the atmosphere was replaced with nitrogen twice. The system was heated to 75° C.~85° C. and stirred for 1~2 hours, filtered while hot, and the filtrate was cooled to 15° C.~20° C. and further stirred for 1~2 hours. Then the reaction product was filtered and drained, washed with a mixture of 0.6 L of isopropanol and 0.4 L of purified water, and then with 0.8 L of purified water to give a wet product. 5.46 L of purified water was added into a 30 L reactor, the wet product was added under stirring, then 1.23 kg of acetic acid and 3.9 L of isopropanol were added, and the atmosphere was replaced with nitrogen twice. 0.08 kg of activated carbon was added, and then the system was heated to 75° C.~85° C. and stirred for 2~3 hours, filtered while hot, and the filtrate was cooled to 15° C.~20° C. and stirred for 0.5~1 hour. Then reaction product was filtered and drained, washed with a mixture of 1 L of isopropyl alcohol and 0.66 L of purified water, then washed with 0.8 L of purified water, dried in vacuum (55° C.~65° C., −0.01 MPa~−0.1 MPa) for 12-16 hours, to give 0.63 kg of off-white solid lenalidomide I, with a yield of 90.1% (total yield of 79.1% based on methyl 2-bromomethyl-3-nitrobenzoate). The product has a HPLC purity of 99.96%, a maximum single impurity of 0.03%, a total heavy metal residue of less than 10 ppm, a metal zinc residue of 5 ppm, and a metal cadmium residue of less than 1 ppm.

Example 3: Preparation Method of Lenalidomide I 550 mL of purified water, acetic acid (243 g, 4.0 mol) and 1.17 L of ethanol were added into a 3 L reactor and stirred. 78 g of lenalidomide intermediate II (0.27 mol, HPLC purity of 99.84%) and iron powder (114 g, 2.04 mol, in which the mass percentage content of metal chromium is about 0.1%) were added into the above reactor, and the atmosphere was replaced with nitrogen twice. The system was heated to 65° C.~75° C. and stirred for 3~4 hours, filtered while hot, and the filtrate was cooled to 15° C.~20° C. and stirred for 1-2 hours. Then the reaction product was filtered and drained, washed with a mixture of 60 mL of ethanol and 40 mL of purified water, and then with 80 mL of purified water to give a wet product. 550 mL of purified water was added into a 3 L reactor, the wet product was added under stirring, then 123 g of acetic acid and 390 mL of ethanol were added, and the atmosphere was replaced with nitrogen twice. 8 g of activated carbon was added, and the system was heated to 65° C.~75° C. and stirred for 1~2 Hours, filtered while hot, and the filtrate was cooled to 15° C.~20° C. and stirred for 0.5 to 1 hour. Then the reaction product was filtered and drained, washed with a mixture of 1 L of ethanol and 0.66 L of purified water, and then with 0.8 L of purified water, dried in vacuum (55° C.~65° C., −0.01 MPa~−0.1 MPa) for 12~16 hours, to give 63.2 g of off-white solid lenalidomide I, with a yield of 90.3% (total yield of 79.4% based on methyl 2-bromomethyl-3-nitrobenzoate). The product has a HPLC purity of 99.96%, a maximum single impurity of 0.04%, a total heavy metal residue of less than 10 ppm, a metal iron residue of 6 ppm, and a metal chromium residue of less than 1 ppm.

Example 4: Preparation Method of Lenalidomide I 550 mL of purified water, formic acid (93 g, 2.0 mol) and 0.55 L of n-propanol were added into a 2 L reactor and stirred. 78 g of lenalidomide intermediate II (0.27 mol, HPLC purity of 99.84%) and zinc powder (62 g, 0.95 mol, in which the mass percentage content of metal cadmium was about 0.1%) were added into the above reactor, and the atmosphere was replaced with nitrogen twice. The system was heated to 70~80° C. and stirred for 2~3 hours, filtered while hot, and the filtrate was cooled to 15° C.~20° C. and stirred for 1~2 hours. Then the reaction product was filtered and drained, washed with a mixture of 60 mL of n-propanol and 40 mL of purified water, and then with 80 mL of purified water to give a wet product. 550 mL of purified water was added into the 3 L reactor, and the wet product was added under stirring, then 123 g of acetic acid and 390 mL of n-propanol were added, and the atmosphere was replaced with nitrogen twice. 8 g of activated carbon were added, and the system was heated to 70° C.~80° C. and stirred for 1~2 hours, filtered while hot, and the filtrate was cooled to 15° C.~20° C. and stirred for 0.5 to 1 hour. Then reaction product was filtered and drained, washed with a mixture of 1 L of ethanol and 0.66 L of purified water, and then with 0.8 L of purified water, dried in vacuum (55° C.~65° C., −0.01 MPa~−0.1 MPa) for 12~16 hours, to give 60.7 g of off-white solid lenalidomide I, with a yield of 86.8% (total yield of 76.2% based on methyl 2-bromomethyl-3-nitrobenzoate). The product has a HPLC purity of 99.95%, a maximum single impurity of 0.03%, a total heavy metal residue of less than 10 ppm, a metal zinc residue of 4 ppm, and a metal cadmium residue of less than 1 ppm.

Example 5: Preparation Method of Lenalidomide I 5.46 L of purified water, propionic acid (2.02 kg, 27.3 mol) and 7.8 L of isopropanol were added into a 30 L reactor and stirred. 0.78 kg of lenalidomide intermediate II (2.70 mol, HPLC purity of 99.84%) and zinc powder (0.79 kg, 12.1 mol, in which the mass percentage content of metal cadmium is about 0.1%) were added into the above reactor, and the atmosphere was replaced with nitrogen twice. The system was heated to 75° C.~85° C. and stirred for 1~2 hours, filtered while hot, and the filtrate was cooled to 15° C.~20° C. and stirred for 1~2 hours. Then the reaction product was filtered and drained, washed with a mixture of 0.6 L of isopropanol and 0.4 L of purified water, and then with 0.8 L of purified water to give a wet product. 5.46 L of purified water was added into a 30 L reactor, and the wet product was added under stirring, then 1.23 kg of acetic acid and 3.9 L of isopropanol were added, and the atmosphere was replaced with nitrogen twice. 0.08 kg activated carbon was added, and the system was heated to 75° C.~85° C. and stirred for 2~3 hours, filtered while hot, and the filtrate was cooled to 15° C.~20° C. and stirred for 0.5~1 hour. Then the reaction product was filtered and drained, washed with a mixture of 1 L of isopropanol and 0.66 L of purified water, and then with 0.8 L of purified water, dried in vacuum (55° C.~65° C., −0.01 MPa~−0.1 MPa) for 12~16 hours, to give 0.62 kg of off-white solid, with a yield of 88.7% (total yield of 77.8% based on methyl 2-bromomethyl-3-nitrobenzoate). The product has a HPLC purity of 99.92%, a maximum single impurity of 0.05%, a total heavy metal residue of less than 10 ppm, a metal zinc residue of 5 ppm and a metal cadmium residue of less than 1 ppm.

Example 6: Preparation Method of Lenalidomide I 5.46 L of purified water, acetic acid (1.64 kg, 27.3 mol) and 7.8 L of isopropanol were added into a 30 L reactor and stirred. 0.78 kg of lenalidomide intermediate II (2.70 mol, HPLC purity of 99.84%) and aluminum powder (0.33 kg, 12.2 mol) were added into the above reactor, and the atmosphere was replaced with nitrogen twice. The system was heated to 75° C.~85° C. and stirred for 1~2 hours, filtered while hot, and the filtrate was cooled to 15° C.~20° C. and stirred for 1~2 hours. Then the reaction product was filtered and drained, washed with a mixture of 0.6 L of isopropanol and 0.4 L of purified water, and then with 0.8 L of purified water to give a wet product. 5.46 L of purified water were added into a 30 L reactor, the wet product was added under stirring, and then 1.23 kg of acetic acid and 3.9 L of isopropanol were added, and the atmosphere was replaced with nitrogen twice. 0.08 kg of activated carbon was added, and the system was heated to 75° C.~85° C. and stirred for 2~3 hours, filtered while hot, and the filtrate was cooled to 15° C.~20° C. and stirred for 0.5~1 hour. Then the reaction product was filtered and drained, washed with a mixture of 1 L of isopropanol and 0.66 L of purified water, and then with 0.8 L of purified water, dried in vacuum (55° C.~65° C., −0.01 MPa~−0.1 MPa) for 12~16 hours, to give 0.63 kg of off-white solid lenalidomide I, with a yield of 90.1% (total yield of 79.1% based on methyl 2-bromomethyl-3-nitrobenzoate). The product has a HPLC purity of 99.91%, a maximum single impurity of 0.05%, a total heavy metal residue of less than 10 ppm, and a metal aluminum residue of 15 ppm.

Example 7: Preparation Method of Lenalidomide I 5.46 L of purified water, acetic acid (1.64 kg, 27.3 mol) and 7.8 L of isopropanol were added into a 30 L reactor and stirred. 0.78 kg of lenalidomide intermediate II (2.70 mol, HPLC purity of 99.84%) and manganese powder (0.67 kg, 12.2 mol) were added into the above reactor, and the atmosphere was replaced with nitrogen twice. The system was heated to 75° C.~85° C. and stirred for 1~2 hours, filtered while hot, and the filtrate was cooled to 15° C.~20° C. and stirred for 1~2 hours. Then the reaction product was filtered and drained, washed with a mixture of 0.6 L of isopropanol and 0.4 L of purified water, and then with 0.8 L of purified water to give a wet product. 5.46 L of purified water was added into a 30 L reactor, and the wet product was added under stirring, then 1.23 kg of acetic acid and 3.9 L of isopropanol were added, and the atmosphere was replaced with nitrogen twice. 0.08 kg of activated carbon was added, and the system was heated to 75° C.~85° C. and stirred for 2~3 hours, filtered while hot, and the filtrate was cooled to 15° C.~20° C. and stirred for 0.5~1 hour. Then the reaction product was filtered and drained, washed with a mixture of 1 L of isopropanol and 0.66 L of purified water, and then with 0.8 L of purified water, dried in vacuum (55° C.~65° C., −0.01 MPa~−0.1 MPa) for 12~16 hours, to give 0.61 kg of off-white solid lenalidomide I, with a yield of 87.3% (total yield of 76.6% based on methyl 2-bromomethyl-3-nitrobenzoate). The product has a HPLC purity of 99.87%, a maximum single impurity of 0.06%, a total heavy metal residue of less than 10 ppm, and a metal manganese residue of 6 ppm.

Comparative Example 1: Preparation Method of Lenalidomide I (According to the Method of Patent Literature WO2011050962)

250 mL of methanol, 12.5 g of lenalidomide intermediate II (0.0456 mol, HPLC purity of 99.84%), and 1.25 g of palladium-carbon catalyst with a mass percentage content of 10% (the mass percentage content refers to the mass percentage content of palladium in the total mass of the palladium-carbon reagent) were added into a 1 L hydrogenation kettle, stirring for 6 to 7 hours under a hydrogen pressure of 3 to 4 atmospheres and a temperature of 35 to 40° C.

The reaction mixture was filtered at 35° C.~40° C., rinsed with 200 mL of methanol, and concentrated in vacuum (35° C.~45° C., −0.05~−0.08 MPa) to remove about 50% of the solvent. The mixture was cooled to room temperature, and additional methanol was added to allow the mixture to be about 300 mL. The mixture was cooled to 0° C.~5° C. and stirred for 1~2 hours, filtered, and washed with 100 mL methanol to give a wet product. 50 mL of water and 7 mL of concentrated hydrochloric acid were added to the wet product, and the mixture was heated to 75° C.~85° C. and stirred for 1~2 hours, then cooled to 5° C.~10° C. and stirred for 0.5~1 hour. Then the reaction product was filtered and drained, washed with 50 mL of water, dried in vacuum (55° C.~65° C., −0.01 MPa~−0.1 MPa) for 12~16 hours, to give 9.35 g of off-white solid crude lenalidomide I, with a yield of 83.5%. The product has a HPLC purity of 99.15%, a maximum single impurity of 0.33%, and a metal palladium residue of 39 ppm.

9.35 g of the crude product of lenalidomide I were added into 280 mL of anhydrous methanol, and the palladium was adsorbed and removed by N-acetyl-L-cysteine, to give 8.42 g of palladium-removed lenalidomide I, with a yield of 90.1% (total yield 66.1%, based on methyl 2-bromomethyl-3-nitrobenzoate). The product has a HPLC purity of 99.15%, a maximum single impurity of 0.33%, and a palladium residue of 3 ppm.

Comparative Example 2: Preparation Method of Lenalidomide I (Prepared According to the Method of Patent Literature WO2011050962 and Purified Using the Methods of Examples 2 to 4)

To 8.42 g of the palladium-removed lenalidomide I product in Comparative Example 1, 16 g of acetic acid and 55 mL of isopropanol were added, and the atmosphere was replaced with nitrogen twice. 0.4 g of activated carbon was added, and the system was heated to 75° C.~85° C. and stirred for 1~2 hours, filtered while hot under 75° C.~85° C., and the filtrate was cooled to 15° C.~20° C. and stirred for 0.5~1 hour. Then reaction product was filtered and drained, washed with a mixture of 40 mL of isopropanol and 30 mL of purified water, and then with 30 mL of purified water, dried in vacuum (55° C.~65° C., −0.01 MPa~−0.1 MPa) for 12~16 hours, to give 7.05 g of off-white solid lenalidomide I, with a yield of 83.7% (total yield of 55.3%, based on methyl 2-bromomethyl-3-nitrobenzoate). The product has a HPLC purity of 99.95%, a maximum single impurity of 0.04%, and a palladium residue of 3 ppm.

Comparative Example 3: Preparation Method of Lenalidomide I 55 mL of purified water, acetic acid (17.0 g, 0.28 mol), and 78 mL of isopropanol were added into a reactor and stirred. 7.8 g of lenalidomide intermediate II (0.027 mol, HPLC purity of 99.84%) and copper powder (7.6 g, 0.12 mol) were added into the above reactor, and the atmosphere was replaced with nitrogen twice. The system was heated to 75° C.~85° C. and stirred for 7~8 hours. No target product lenalidomide I was found. The result shows that the target compound can be hardly obtained where the metal is selected from copper.

Comparative Example 4: Preparation Method of Lenalidomide I 55 mL of purified water, lactic acid (25.2 g, 0.28 mol), and 78 mL of isopropanol were added into a reactor and stirred.

7.8 g of lenalidomide intermediate II (0.027 mol, HPLC purity of 99.84%) and zinc powder (7.9 g, 0.12 mol) were added to the above reactor, and the atmosphere was replaced with nitrogen twice. The system was heated to 75° C.~85° C. and stirred for 7~8 hours. No target product lenalidomide I was found. The result shows that the target compound can be hardly obtained where the organic acid is selected from lactic acid.

The foregoing description of various embodiments of the present disclosure has been presented for the purposes of illustration and description. It should be understood that the present disclosure is not limited to the above-mentioned embodiments. Any modification, equivalent replacement, improvement, etc. made within the spirit and principle of the present invention shall be included in the protection scope defined by the claims appended hereto.

The invention claimed is:

1. A method for preparing lenalidomide I, comprising:
subjecting a lenalidomide intermediate II to a reduction reaction to obtain the lenalidomide I in the presence of an organic acid and a metal in a first solvent at a temperature of 55° C.-95° C. for 1 hr-5 hrs:

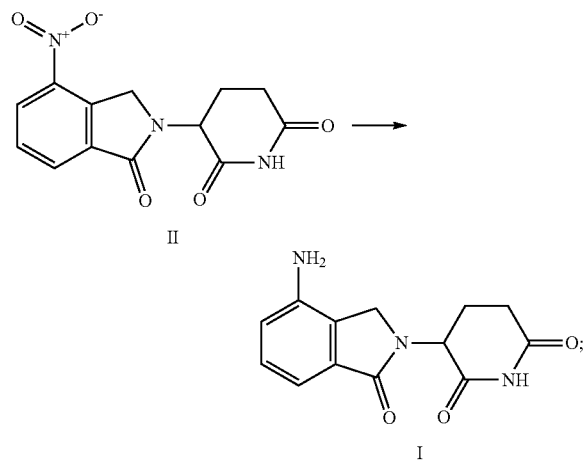

filtering to obtain a first filtrant, cooling and crystalizing the first filtrant to form a first solid, washing the first solid to obtain a crude lenalidomide I;
adding the crude lenalidomide I, activated carbon, and acetic acid in a second solvent to form a mixture;
heating the mixture to dissolve the crude lenalidomide I;
filtering the mixture to obtain a second filtrant, cooling and crystalizing the second filtrant to obtain a second solid, washing and drying the second solid to obtain the lenalidomide I having an HPLC purity of higher than 99.90%, wherein:
the first solvent comprises a first alcohol and water at a volume ratio of 0.5-3, the first alcohol being selected from methanol, ethanol, isopropanol, n-propanol, n-butanol, and mixtures thereof,
the organic acid is selected from formic acid, acetic acid, propionic acid, and mixtures thereof, the metal is one or more selected from zinc, iron, aluminum, and manganese,
a volume-mass ratio between the first solvent and the lenalidomide intermediate II is 10 ml/g-25 ml/g, a molar ratio between the metal and the lenalidomide intermediate II is 3-8, and a molar ratio between the organic acid and the lenalidomide intermediate II of 7-15,
the second solvent comprises a second alcohol and water, the second alcohol being selected from methanol, ethanol, isopropanol, n-propanol, n-butanol, and mixtures thereof,
a volume-mass ratio between the second solvent and the lenalidomide intermediate II is 1 mL/g-50 mL/g, a mass ratio between the activated carbon and the lenalidomide intermediate II is 0.01-1, and a molar ration between acetic acid to the lenalidomide intermediate II is 1-10.

2. The method for preparing lenalidomide I according to claim 1, wherein the lenalidomide I has a maximum single impurity of 0.10%.

3. The method for preparing lenalidomide I according to claim 2, wherein the lenalidomide has a heavy metal content of less than 10 ppm.

4. The method for preparing lenalidomide I according to claim 1, wherein a yield of the lenalidomide I from the lenalidomide intermediate II is 76.2% to 79.4%.

5. The method for preparing lenalidomide I according to claim 1, wherein the first solvent consists of the first alcohol and water.

6. The method for preparing lenalidomide I according to claim 5, wherein the reduction reaction is carried out at a temperature of 60° C. to 90° C.

7. The method for preparing lenalidomide I according to claim 1, wherein the first solid, the second solid, or both are washed with an alcohol solvent and/or water.

8. The method for preparing lenalidomide I according to claim 7, wherein the mixture is maintained at a temperature of 55° C. to 95° C.

9. The method for preparing lenalidomide I according to claim 8, wherein the second filtrant is maintained at a temperature of −5° C. to 35° C. for a duration of 0.1 to 5 hours.

* * * * *